United States Patent [19]

Rivas et al.

[11] Patent Number: 5,710,093

[45] Date of Patent: Jan. 20, 1998

[54] HYDROGENATION CATALYST WITH IMPROVED ATTRITION RESISTANCE AND HEAT DISSIPATION

[75] Inventors: Luis A. Rivas; Enzo Peluso, both of Miranda; Daisy Rojas; Juan Jose Garcia, both of Caracas, all of Venezuela

[73] Assignee: Intevep, S.A., Caracas, Venezuela

[21] Appl. No.: 718,020

[22] Filed: Sep. 20, 1996

Related U.S. Application Data

[60] Division of Ser. No. 399,239, Mar. 6, 1995, Pat. No. 5,648,312, which is a continuation-in-part of Ser. No. 366,265, Dec. 29, 1994, abandoned.

[51] Int. Cl.[6] .................... C11D 21/06; C11D 21/08; C11D 27/224
[52] U.S. Cl. .................... 502/439; 502/178; 502/239; 502/242; 502/258; 502/259; 502/260
[58] Field of Search .................... 502/439, 178, 502/239, 242, 258, 259, 260, 325, 326, 337, 349

[56] References Cited

U.S. PATENT DOCUMENTS

| | | | |
|---|---|---|---|
| 4,818,732 | 4/1989 | Fox et al. | 501/81 |
| 4,857,497 | 8/1989 | De Jong et al. | 502/242 |

*Primary Examiner*—Glenn Caldarola
*Assistant Examiner*—Alexander G. Ghyka
*Attorney, Agent, or Firm*—Bachman & LaPointe, P.C.

[57] ABSTRACT

A catalyst support includes substantially spherical particles of a substantially homogeneous mixture of at least two compounds selected from the group consisting of refractory inorganic oxides, refractory inorganic carbides, refractory inorganic nitrides and mixtures thereof, wherein said particles have a surface area of at least about 30 $m^2/g$, an average pore diameter of at least about 150 Å, and a particle size of at least about 0.1 mm. The support may be used in a catalyst system to support a Group IVb and a Group VIII metal in a catalyst system useful for hydrogenation of carbon monoxide into $C_2+$ hydrocarbons. A method is also provided for preparing the catalyst support and system.

22 Claims, 1 Drawing Sheet

HYDROGENATION CATALYST WITH IMPROVED ATTRITION RESISTANCE AND HEAT DISSIPATION

This is a Division of application Ser. No. 08/399,239 now U.S. Pat. No. 5,648,312 filed Mar. 6, 1995, which is a Continuation-In-Part of application Ser. No. 08/366,265 filed Dec. 29, 1994, now abandoned.

BACKGROUND OF THE INVENTION

The invention relates to a hydrogenation catalyst. Specifically, the invention relates to a catalyst having improved attrition resistance and heat dissipation properties which is particularly useful in the hydrogenation of a carbon monoxide feedstock so as to obtain $C_2+$ hydrocarbon products.

Numerous patents contain disclosures of processes for hydrogenation reactions wherein carbon monoxide is upgraded to desirable hydrocarbon products. One method of performing this hydrogenation is to induce a Fischer Tropsch reaction, wherein carbon monoxide is converted in an exothermic reaction to the desired end product.

Numerous types of reactors can be used for carrying out the hydrogenation reaction. One type is known as an ebulliating bed reactor. An ebulliating bed reactor is characterized by a vessel containing a bed of the catalyst through which the feedstock is passed, typically from the bottom toward the top of the reactor. This results in a bed of the catalyst suspended in the medium and subjected to continuous collisions. The catalyst itself remains inside the reactor.

One problem encountered in the art with ebulliating reactors is the attrition rate of the catalyst contained in the reactor. That is, the catalyst tends to break down to smaller particles or fines after any significant amount of use.

It is therefore a primary object of the present invention to provide a catalyst system wherein the catalyst particles are resistant to attrition.

It is a further object of the present invention to provide a catalyst having good heat dissipation properties so as to assist in dissipating heat generated by the exothermic hydrogenation reaction.

It is a still further object of the present invention to provide a catalyst system which has excellent activity and selectivity toward desirable hydrogenation reactions for converting a carbon monoxide feedstock to $C_2+$ hydrocarbons.

It is another object of the present invention to provide a process for preparing a catalyst system according to the invention.

It is still another object of the present invention to provide a process for hydrogenation of carbon monoxide to $C_2+$ hydrocarbons using the catalyst of the present invention.

Other objects and advantages of the invention will appear hereinbelow.

SUMMARY OF THE INVENTION

In accordance with the invention, the foregoing objects and advantages are readily attained.

In accordance with the invention, a catalyst support is provided which comprises substantially spherical particles of a substantially homogeneous mixture of at least two compounds selected from the group consisting of refractory inorganic oxides, refractory inorganic carbides, refractory inorganic nitrides and mixtures thereof, wherein said particles have a surface area of at least about 30 $m^2/g$, an average pore diameter of at least about 150 Å, and a particle size of at least about 0.1 mm.

In further accordance with the invention, a catalyst system for hydrogenation of carbon monoxide feedstock is provided which comprises a catalyst support comprising substantially spherical particles of a substantially homogeneous mixture of at least two compounds selected from the group consisting of refractory inorganic oxides, refractory inorganic carbides, refractory inorganic nitrides and mixtures thereof, wherein said particles have a surface area of at least about 30 $m^2/g$, an average pore diameter of at least about 150 Å, and a particle size of at least about 0.1 mm, and a catalytically active metal phase supported on said support and comprising at least one metal selected from the group consisting of Group IVb metals, Group VIII metals, and mixtures thereof.

The catalytically active phase may preferably comprise a first metal selected from Group IVb, preferably zirconium, and a second metal selected from Group VIII, preferably cobalt.

In further accordance with the present invention, a method for preparing the catalyst support of the present invention is provided which comprises the steps of forming a suspension comprising particles of at least two compounds selected from the group consisting of refractory inorganic oxides, refractory inorganic carbides, refractory inorganic nitrides, and mixtures thereof in a basic aqueous solution, adding a pore size controlling agent to the suspension, forming droplets of the suspension, passing the droplets through an inert organic liquid phase so as to form the droplets into spheres, passing the spheres through an aqueous acidic solution so as to provide at least partially solidified spheres of said catalyst support.

In further accordance with the invention a method is provided for production $C_2+$ hydrocarbons by hydrogenation of carbon monoxide, which method comprises the steps of providing a catalyst system comprising a catalyst support comprising substantially spherical particles of a substantially homogeneous mixture of at least two compounds selected from the group consisting of refractory inorganic oxides, refractory inorganic carbides, refractory inorganic nitrides and mixtures thereof, wherein said particles have a surface area of at least about 30 $m^2/g$, an average pore diameter of at least about 150 Å, and a particle size of at least about 0.1 mm, and a catalytically active metal phase supported on said support and comprising at least one metal selected from the group consisting of Group IVb metals, Group VIII metals, and mixtures thereof, reducing said catalyst system under a hydrogen atmosphere, providing a CO feedstock, and contacting said CO feedstock and said catalyst system in the presence of reaction hydrogen under hydrogenation conditions so as to produce $C^2+$.

BRIEF DESCRIPTION OF THE DRAWINGS

A detailed description of the preferred embodiments of the invention follows, with reference to the attached drawings wherein.

DETAILED DESCRIPTION

The invention relates to a hydrogenation catalyst support and system, methods for preparing the catalyst system and support in accordance with the invention, and a method for hydrogenation of a carbon monoxide feedstock so as to provide $C^{2+}$ products using the catalyst system according to the invention.

According to the invention, a catalyst support is provided which is useful in a catalyst system for hydrogenation of carbon monoxide feedstocks. The catalyst support according to the invention has enhanced resistance to attrition when used in an ebulliating bed reactor, and further has enhanced heat dissipation qualities which is desirable in light of the exothermic nature of the hydrogenation reaction to be carried out in accordance with the invention.

The catalyst support of the present invention is provided in the form of substantially spherical particles of a substantially homogeneous mixture of at least two compounds selected from the group consisting of refractory inorganic oxides, refractory inorganic carbides, refractory inorganic nitrides and mixtures thereof. The particles preferably are made up of a mixture of a refractory inorganic oxide and a refractory inorganic carbide, most preferably a mixture of silica and silicon carbide.

Figure 1:
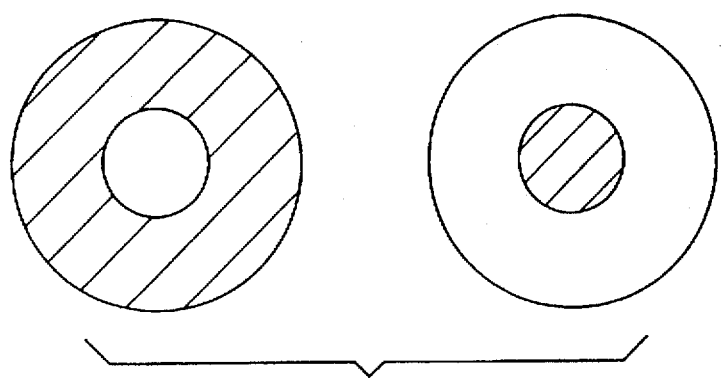
FIG. 1 illustrates prior art particles having silicon carbide and silica.
Figure 2:
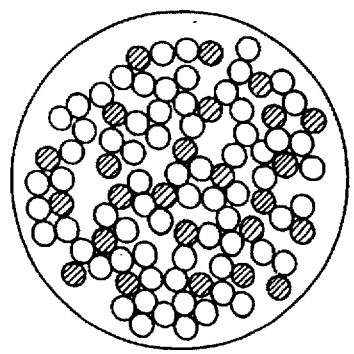
FIG. 2 illustrates a particle comprising an aggregate of particles of silicon carbide and silica in accordance with the invention.

In further accordance with the invention, the particles comprise a substantially homogeneous aggregate mixture of the silica and silicon carbide. Referring to FIG. 1, it is known in the art to provide a substrate of one or the other of silica and silicon carbon and to deposit a coating of the other over the substrate, as is shown in FIG. 1 wherein the shaded portion is silicon carbide and the non-shaded portion is silica. Referring to FIG. 2, an aggregate of silica and silicon carbide according to the invention is illustrated. As clearly shown, the particles according to the present invention are significantly different from that of the prior art. Further, the aggregate structure of the catalyst support of the present invention has been found to provide enhanced resistance to attrition in an ebulliating bed reactor and further provides for excellent activity and selectivity of a catalyst system using the catalyst support of the present invention.

According to the invention, the particles of catalyst support preferably have a surface area of at least about 30 m²/g, most preferably at least 40 m²/g. Further, the particles preferably have an average pore diameter of at least about 150 Å, more preferably of between about 200 to about 500 Å. Further, the catalyst support according to the present invention preferably has a pore diameter distribution such that at least about 60% of the individual pore diameters of the particles are greater than about 150 Å. Most preferably, at least about 80% of the individual pore diameters are greater than about 150 Å.

The catalyst support of the present invention is further characterized by a particle size of at least about 0.1 mm, preferably between about 0.1 to about 3.0 mm, and most preferably between about 0.1 to about 1.0 mm.

In further accordance with the invention, the catalyst support is preferably provided having silicon carbide present in an amount of between about 10% to about 50% by weight of the catalyst support. In increasing order of preference, the silicon carbide may be present in the catalyst support particles in an amount of between about 10–35, 15–30, and 15–26% by weight of the catalyst support.

The catalyst support of the present invention is further characterized by a pore volume of between about 0.2 cc/g to about 1.2 cc/g, more preferably between about 0.25 to about 0.60 cc/g.

In accordance with the invention, the for&going catalyst support having the aforementioned physical characteristics has been found not only to have excellent activity and selectivity in hydrogenation reactions, but further has enhanced resistance to attrition and improved heat dissipation properties.

In further accordance with the invention, the aforedescribed catalyst support may be loaded, impregnated, or otherwise provided with a catalytically active metal phase so as to provide the catalyst system according to the invention. The hydrogenation catalyst system of the present invention preferably has at least one metal selected from Group IVb and Group VIII of the periodic table of elements, and more preferably has at least two metals, one selected from each of Group IVb and Group VIII. The Group IVb metal is preferably selected from the group consisting of zirconium, titanium, hafnium, and mixtures thereof, most preferably zirconium. The Group VIII metal is preferably selected from the group consisting of cobalt, iron, nickel, ruthenium, and mixtures thereof, most preferably cobalt.

According to the invention, the Group IVb metal is preferably present in an amount of between about 0.01% to about 25%, preferably 0.01 to about 5% by weight, with respect to the catalyst system. The Group VIII metal is preferably provided in an amount of between about 1% to about 50%, preferably 6% to 25% by weight with respect to the catalyst system. Further, the Group IVb and Group VIII metals are preferably provided in a weight ratio of Group IVb metal to Group VIII metal of between about 25:1 to about 1:8000.

Of course, the catalyst support according to the present invention may be provided with numerous combinations of catalytically active metals, particularly dependent upon the process for which the catalyst system is to be used, the feedstock to be treated and the desired end products. Further, although the present embodiment is disclosed in terms of zirconium and cobalt supported on the catalyst support, it should be appreciated that combinations of more than two metals could of course be used if desired.

The combination of zirconium and cobalt as set forth above and in the proportions as set forth above has been found according to the invention to provide excellent activity and selectivity in the hydrogenation of carbon monoxide feedstocks so as to provide $C^{2+}$ products.

According to the invention a method is also provided for preparing the catalyst support and catalyst system of the present invention. In accordance with the method of the present invention, the aforedescribed catalyst support and system are provided having the desired spherical particles of substantially homogeneous mixture of silica and silicon carbide. The present method is instrumental in providing the desired homogeneous mixture or aggregate of silica and silicon carbide as illustrated in FIG. 2, rather than the substrate with deposited component structure as illustrated in FIG. 1 which is obtained in accordance with the prior art.

According to the invention, the catalyst support of the present invention may be provided by forming a suspension of particles of the desired compound selected from the group consisting of refractory inorganic oxides, refractory inorganic carbides, refractory inorganic nitrides, and mixtures thereof in a basic aqueous solution. In accordance with the invention, a pore size controlling agent is preferably then added to the suspension so as to induce the formation of the appropriate pore size in the suspension. Next, droplets of the suspension are formed and passed through an inert organic liquid phase which may preferably include an anionic surfactant which acts to form the droplets of suspension into spheres. The spheres of suspension are then passed in accordance with the method of the present invention through an aqueous acidic solution which serves to gel or at least partially solidify these spheres so as to provide spherical particles of the desired substantially homogeneous mixture or aggregate of the silica and silicon carbide compounds.

In accordance with the invention, the suspension of support compounds may be formed by providing a silica suspension or aquasol such as Ludox AS40 which is provided by DuPont, preferably at a pH of between about 9 to about 10. Particles of silicon carbide may then be added to the silica suspension. The particles of compounds to be provided in the suspension preferably have a particle size of less than or equal to about 150 microns, preferably less than or equal to about 50 microns.

Numerous additives may be utilized, if desired, to provide the desired basic pH of the solution in which the suspension is formed. The actual agent used to provide the pH forms no part of the present invention.

The viscosity of the suspension may be adjusted in accordance with the present invention so as to maintain the particulate compounds in suspension during the catalyst forming method. In accordance with the present invention, the viscosity controlling agent may be added to the suspension so as to provide a viscosity of at least about 50 cp at 25° C., thereby maintaining the silica and silicon carbide particles in suspension while the support is being formed. Numerous viscosity controlling agents may be used in accordance with conventional techniques. An example of a suitable viscosity controlling agent is ethylene oxide polymer such as Polyox WSR-205, supplied by Union Carbide.

In accordance with the invention, a pore forming agent is then added to the suspension so as to provide the desired pores and pore size in the suspension which result in the catalyst support having the desired pore size characteristics as discussed above. Suitable pore inducing or size controlling agents include hexamethylenetetramine, urea, water soluble starch, and mixtures thereof. The preferred pore size controlling agent is hexamethylenetetramine.

The slurry of suspension and pore size controlling agent is then preferably formed into droplets in accordance with the invention, which droplets preferably have a size of between about 0.1 mm to about 3.0 mm.

The desired droplets of suspension may be formed in accordance with the invention using any known technique or equipment, such as, for example a spinning disk atomizer or the like. Of course, numerous methods and apparatus are known in the art for providing droplets of a liquid phase, and the exact method or apparatus used forms no part of the present invention.

In further accordance with the method for preparing the catalyst support of the present invention, the formed droplets of desired size are then passed sequentially first through an inert organic liquid phase and then through an aqueous acidic solution. The sequential passing of droplets through the aforementioned phases serves to provide the droplets of suspension with the desired spherical shape, and then to gel or at least partially solidify the spherical droplets for final treatment steps such as calcining and the like so as to provide the desired spherical particles of substantially homogeneous mixture of silica and silicon carbide in accordance with the invention.

The inert organic liquid phase may suitably be kerosene, hexane, toluene, mineral oil, vegetable oil, alcohol, and mixtures thereof, and may in accordance with the invention further include an anionic surfactant to enhance the sphere forming nature of the inert organic phase.

The aqueous acidic solution which induces the gelling of spheres of the catalyst support in accordance with the invention preferably has a pH of between about 4 to about 5. Any of numerous additives may be provided in the aqueous solution so as to reduce the pH to the desired level. As the droplets pass from the first solution in spherical form, the second solution or phase stabilizes the spheres as the gelification process is initiated.

In accordance with the invention, the first inert organic phase and the second aqueous acidic solution phase may be provided in a vessel having the first phase as an upper phase and the second phase as a lower phase whereby droplets formed from the suspension may be passed sequentially through the first phase and then the second phase by allowing the droplets to sink through the vessel. Of course, separate vessels may be provided for containing each of the first or second phase and numerous other configurations may be provided for passing the droplets sequentially through the first and second phases so as to provide the at least partially solidified spheres of substantially homogeneous mixture or aggregate of silica and silicon carbide as desired.

In further accordance with the invention, the spheres obtained from the aqueous acidic solution are then preferably dried, calcined, and hydrothermally treated so as to provide the desired average pore diameter and pore diameter distribution which, in accordance with the invention, serve to provide the catalyst support with the desired physical characteristics which have been found in accordance with the invention to be particularly suitable for hydrogenation of carbon monoxide.

According to the invention, the at least partially solidified spheres obtained from the aqueous acidic solution are preferably first dried in a conventional drying step so as to provide dry spherical particles of the catalyst support.

The dry spherical particles are then preferably calcined at a temperature of between about 350° to about 600° C. The calcination is preferably carried out for a period of time sufficient to remove all traces of solvents and additives and thereby provide the desired solid spheres of silica and silicon carbide in a substantially homogeneous mixture or aggregate in accordance with the invention.

The calcined spherical particles may then be hydrothermally treated at an elevated temperature which serves to collapse the smallest pores of the particles so as to increase the average pore diameter to at least about 150 Å, and preferably to between about 200 to about 500 Å.

After hydrothermal treatment, the catalyst support is then preferably calcined again at a temperature of between about 350° to about 600° C. so as to provide the desired catalyst support having a surface area of at least about 30 m²/g, a particle size of at least about 0.1 mm, and a pore volume of between about 0.2 cc/g to about 1.2 cc/g.

The hydrothermal treatment and calcining steps are preferably carried out so as to provide the catalyst support with a pore size distribution wherein at least about 60%, and preferably at least about 80% of individual pore diameters are greater than about 150 Å.

The aforementioned hydrothermal treatment and calcining steps are carried out in accordance with known techniques which form no part of the present invention.

In further accordance with the invention, the catalyst support provided in accordance with the above-identified method may then be provided with a catalytically active metal phase so as to provide a catalyst system, preferably for use in hydrogenation of a carbon monoxide feedstock. The catalyst support may be incorporated into a catalyst system according to the invention by supporting a catalytically active metal phase having at least one metal selected from Group IVb and Group VIII of the periodic table of elements. The catalytically active metal phase, as set forth above, preferably includes at least two metals from the above-mentioned groups, most preferably one Group IVb metal and one Group VIII metal. The metals may be supported on the catalyst support through any conventional procedure or technique such as sequential or simultaneous impregnation, ion exchange, or any other suitable procedure.

In accordance with the invention, the metal may be provided on the support through impregnation of aqueous solutions containing the desired metal. Suitable aqueous solutions may be formed by mixing a water soluble salt of the desired metal in water. Suitable salts include nitrates, oxalates, sulphates, acetates, acetylacetanates, and mixtures thereof.

The catalyst support provided in accordance with the method of the present invention has been found, in accordance with the present invention, to be particularly well suited to hydrogenation of carbon monoxide into desirable and more valuable $C_2+$ hydrocarbon products. In accordance with the present invention, the process for treating carbon monoxide with the catalyst system of the present invention comprises the steps of providing a catalyst system including the catalyst support according to the invention and a catalytically active metal phase supported on the support, preferably in a suitable reactor such as an ebulliating bed reactor. The catalyst system is preferably reduced under a hydrogen atmosphere in accordance with the invention so as to provide the catalyst system in the appropriate state for hydrogenation. In accordance with the invention, a carbon monoxide feedstock is provided and preferably mixed with reaction hydrogen to form a reaction feedstock which is contacted with the reduced catalyst system whereby the carbon monoxide feedstock is hydrogenated so as to provide desirable $C_2+$ hydrocarbon products.

The reaction feedstock and catalyst system are of course contacted under hydrogenation conditions which are suitable and effective for carrying out the hydrogenation reaction. The hydrogenation conditions are preferably standard Fischer Tropsch conditions suitable to produce $C_2+$ hydrocarbons. Typical hydrogenation conditions include, for example, a temperature of about 220° C., pressure of about 230 psig, GSHV of about 500 $H^{-1}$, and a ratio of hydrogen to carbon monoxide feedstock of about 2, although of course the conditions vary depending upon the feedstock and the desired reaction products.

In accordance with the invention, the catalyst support exhibits an excellent resistance to attrition when used in an ebulliating bed reactor. When arranged in such a reactor, for example, the catalyst system of the present invention exhibits a bed strength of 20 kg/cm$^2$ and produces only 0.1% of fine particles having a particle size less than 250 microns. This represents a substantial improvement over conventional catalyst systems for use in ebulliating bed reactors. Furthermore, the refractory nature of the silicon compounds of the catalyst support of the present invention serve to provide improved heat dissipation characteristics which are useful in the exothermic conditions of the hydrogenation treatment for which the catalyst system is used.

The following examples illustrate the features of the catalyst support, catalyst system, method for preparation and method for use of the catalyst support and system for hydrogenation of carbon monoxide in accordance with the invention.

EXAMPLE 1

This example illustrates the preparation of a catalyst support in accordance with the method of the present invention. Four slurries were prepared by mixing 1092 ml. of a silica aquasol (Ludox AS40 at pH 10, DuPont) with four different amounts of silicon carbide having a particle size of less than or equal to 30 microns. Ethylene oxide polymer (Polyox WSR-205, Union Carbide) was added to the suspension at a concentration of 300 ppm so as to adjust the viscosity of the suspension or slurry to a value exceeding 50 cp at 25° C. A pore forming agent, hexamethylenetetramine, was then added to the suspension. The suspension was then delivered by spinning disk atomizer to a vessel containing a two phase liquid having an upper phase composed of kerosene and an anionic surfactant and a lower phase containing an aqueous buffer with a pH which was maintained between about 4 to about 5. As the formed droplets sink through the organic phase, the droplets attain a spherical form which is stabilized by the presence of the anionic surfactant. When the spherical droplets of slurry or suspension enter the acidic phase, the gelification process initiates so as to stabilize and at least partially solidify the spherically formed droplets of suspension. The spheres were then recovered and dried overnight at 40°. The dried spheres were then calcined at 500° C. so as to remove all traces of solvent and additive. The spheres were then hydrothermally treated at 180° C. so as to increase the average pore diameter of the spheres, which were then calcined again at 500° C. The resulting spherical particles had an average particle size of about 0.65 mm.

Four catalyst supports were prepared from the slurries in accordance with the above procedure, each having a different weight percentage of silicon carbide. The characteristics of each support are set forth below in Table I.

TABLE I

| SUP-PORT | SiC WT % | SURFACE AREA m²/g | PORE VOLUME cm³/g | PORE DIAMETER Å | Pore Diameter Distribution (%) | |
|---|---|---|---|---|---|---|
| | | | | | <150 Å | >150 Å |
| 1 | 0 | 48 | 0.42 | 350 | 6.58 | 93.42 |
| 2 | 15 | 51 | 0.41 | 322 | 15.12 | 84.88 |
| 3 | 26 | 40 | 0.42 | 420 | 4.36 | 95.64 |
| 4 | 35 | 40 | 0.41 | 410 | 6.32 | 93.68 |

As set forth in Table I, the method for providing the catalyst support in accordance with the invention results in the catalyst support having physical characteristics such as surface area, pore volume, average pore diameter and pore diameter distribution all within the desired ranges as set forth in the invention.

EXAMPLE 2

This example illustrates the preparation of a catalyst system wherein the catalyst support of Example 1 is impregnated with zirconium and cobalt. The four samples of catalyst support prepared in Example 1 were co-impregnated with the desired active metals using a pore saturation method with solutions containing $ZrONO_3.H_2O$ and $Co(NO_3)_2.H_2O$. The catalysts were prepared so as to contain 8% by weight of cobalt and 1% by weight of zirconium. The impregnated supports were dried at 260° C. and calcined at 360° C. to oxidize the metal phase. Table II set forth below contains the physical characteristics of each catalyst system prepared from supports 1–4 of Example 1.

TABLE II

| CATA-LYST | SUP-PORT | SURFACE AREA m²/g | PORE VOLUME cm³/g | PORE DIAMETER Å | Pore Diameter Distribution (%) | |
|---|---|---|---|---|---|---|
| | | | | | <150 Å | >150 Å |
| A | 1 | 46 | 0.35 | 304 | 14.88 | 85.12 |
| B | 2 | 50 | 0.34 | 272 | 7.31 | 92.69 |
| C | 3 | 40 | 0.36 | 360 | 13.58 | 86.42 |
| D | 4 | 41 | 0.34 | 331 | 7.59 | 92.41 |

EXAMPLE 3

This example illustrates the effect of the composition of the catalyst support on the activity of the catalyst system based thereon. Catalyst systems A–D as set forth in Table II above were provided having an average particle size of about 0.8 mm and used to hydrogenate a carbon monoxide feedstock at a temperature of 220° C., a pressure of 230 psig, a ratio of hydrogen to carbon monoxide of 2, and a GHSV of 500 $H^{-1}$. The results of each reaction, carried out in a fixed bed reactor, are set forth below in Table III.

TABLE III

| | CATALYST | | | |
|---|---|---|---|---|
| | A | B | C | D |
| % SiC | 0 | 15 | 26 | 35 |
| CONVERSION | 81 | 81 | 80 | 82 |
| PRODUCTS: (% mol) | | | | |
| $CH_4$ | 10 | 11 | 8 | 8 |
| $C_2+$ | 85 | 86 | 89 | 90 |
| $CO_2$ | 5 | 3 | 3 | 2 |

As shown in Table III, the conversion of carbon monoxide remains substantially the same regardless of the concentration of silicon carbide in the support. However, the selectivity of the catalyst toward $C_2+$ hydrocarbons increased with the increase in concentration of silicon carbide.

EXAMPLE 4

This example illustrates the effect of the particle size of the catalyst system on the activity and selectivity of the catalyst when used in hydrogenation reactions. Three catalyst systems (E, F, G), were prepared containing 26% by weight silicon carbide in accordance with the procedure of Example 1. The catalyst supports were prepared having particle sizes ranging between 0.65 mm to 2.5 mm. Each support was impregnated as in Example 2 with 8% weight cobalt and 1% weight zirconium. Each catalyst was used in a hydrogenation procedure of a carbon monoxide feedstock at a temperature of 223° C., a pressure of 300 psig, a hydrogen to carbon monoxide ratio of 2, GHSV of 500 $H^{-1}$, and a paraffin flow of 60 cc/min. The reactions were carried out in an ebulliating bed reactor, and the results are set forth below in Table IV.

TABLE IV

| | CATALYST | | |
|---|---|---|---|
| | E | F | G |
| SIZE (mm) | 2.5 | 1.8 | 0.65 |
| CONVERSION | 37 | 57 | 56 |
| PRODUCTS: (% mol) | | | |
| $CH_4$ | 23 | 22 | 9 |
| $CH_2+$ | 76 | 77 | 89 |
| $CO_2$ | 1 | 1 | 2 |

As shown, the particle size of 0.65 yielded the highest selectivity to $C_2+$ hydrocarbon products as desired. Further, conversion increased as the particle size decreased from 2.5 mm.

EXAMPLE 5

This example illustrates the effect of the surface area of the catalyst of the present invention on its activity when used in hydrogenation reactions. Two catalyst (H, I), were prepared as described in Example 2 having 12% weight cobalt and 1.5% weight zirconium. Catalyst H was calcined as described in Example 2 while Catalyst I was calcined at a temperature of 850° C. so as to obtain a smaller surface area. A reaction was then carried out in a fixed bed reactor under the reaction conditions set forth in Example 3, and the results are set forth below in Table V.

TABLE V

| CATA-LYST | SURFACE AREA m²/g | CONVERSION % | PRODUCTS (% mol) | | |
|---|---|---|---|---|---|
| | | | $CH_4$ | $C_2+$ | $CO_2$ |
| H | 40 | 80 | 8 | 89 | 3 |
| I | 21 | 42 | 16 | 80 | 4 |

As shown, the decrease in surface area adversely effects both activity and selectivity of the catalyst. The smaller surface area causes a shift in reaction products towards undesirable $CO_2$ and $C_4$ and away from the desirable $C_2+$ products.

EXAMPLE 6

This example illustrates the effect of the pore diameter of the catalyst system of the present invention on the conversion of CO and hydrogenation reactions. Three catalysts (H as in Example 5 above, P and J) were prepared as described in Example 2 and loaded with 12% weight Cobalt and 1.5% weight zirconium. Catalysts P and J were not subjected to varying hydrothermal treatments so as to provide smaller pore diameter as set forth below in Table VI. Each catalyst system was then used in a hydrogenation reaction procedure as described in Example 3. The results of the reactions are also set forth below in Table VI.

TABLE VI

| CATALYST | PORE DIAMETER Å | PRODUCTS (% mol) | | |
|---|---|---|---|---|
| | | CH$_4$ | C$_2$+ | CO$_2$ |
| H | 270 | 9 | 86 | 5 |
| P | 150 | 19 | 77 | 4 |
| J | 11 | 58 | 2 | 40 |

As shown, the decrease in pore diameter out of the preferred range in accordance with the present invention caused a shift of the product of the hydrogenation reaction away from the desirable C$_2$+ products and toward undesirable CH$_4$ and CO$_2$ products.

EXAMPLE 7

This example illustrates the effect of the cobalt and zirconium concentrations of the catalyst system on the conversion of carbon monoxide. Six catalyst systems were prepared as described in Example 2, each with differing concentrations of cobalt and/or zirconium as set forth below in Table VII. The catalysts used in this example were Catalyst H as discussed in Example 5 above, and Catalysts K, L, M, N and O each having the concentration of cobalt and zirconium as listed below in Table VII. Each catalyst was used in a carbon monoxide hydrogenation reaction as described in Example 3, with the results of the reaction also being set forth below in Table VII.

TABLE VII

| | CATALYST | | | | | |
|---|---|---|---|---|---|---|
| | H | K | L | M | N | O |
| Co % wt | 12 | 8 | 20 | 25 | 16 | 6 |
| Zr % wt | 1.5 | 1.0 | 10 | 3 | 5 | 0.001 |
| Conversion % | 96 | 85 | 95 | 98 | 74 | 58 |
| Products: % mol | | | | | | |
| CH$_4$ | 9 | 7 | 12 | 13 | 9 | 8 |
| C$_2$+ | 86 | 92 | 82 | 79 | 90 | 90 |
| CO$_2$ | 5 | 1 | 6 | 8 | 1 | 2 |
| C$_4$–/C$_4$ | 0.25 | — | 0.19 | — | — | 0.86 |

In accordance with the invention, zirconium in the catalyst serves to improve the selectivity of the catalyst toward the production of paraffins.

EXAMPLE 8

This example illustrates the resistance of a catalyst system in accordance with the invention to attrition when used in an ebulliating bed reactor. A support was prepared as described above in Example 1 and provided with a particle size of 0.65 mm. The support was placed in a column having 100 cm in height and an internal diameter of 4 cm. The column was filled with 100 cm$^3$ of the support and an air/water mixture was injected into the bottom of the column at room temperature for 30 days. The air was fed at 1300 H$^{-1}$ with a speed of 191 cm/min., while the water was fed at 240 H$^{-1}$ at a speed of 32 cm/min. After 30 days of operation, the fine production measured in the terms of particulate having a size smaller than 250 microns was less than 7% weight of the catalyst support, which demonstrates an excellent resistance to attrition.

Thus provided is an improved catalyst support and catalyst system which exhibits enhanced resistance to attrition, improved heat dissipation qualities, and an excellent activity and selectivity in the hydrogenation of carbon monoxide so as to provide C$_2$+ hydrocarbon products. Further, a method is provided in accordance with the invention for preparing the catalyst support and system having the desired physical characteristics which have been found in accordance with the invention to be instrumental in providing the above-identified advantages of the catalyst in accordance with the present invention. Also provided is a method for hydrogenating a carbon monoxide feedstock using the catalyst system of the present invention so as to convert the carbon monoxide feedstock into desirable and more valuable C$_2$+ hydrocarbon products.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A method for preparing a catalyst support, comprising the steps of:

forming a suspension consisting of silicon carbide and silica in a basic aqueous solution;

adding a pore size controlling agent to the suspension;

forming droplets of the suspension;

passing the droplets through an inert organic liquid phase so as to form the droplets into spheres;

passing the spheres through an aqueous acidic solution so as to provide at least partially solidified spheres of said catalyst support containing a substantially homogeneous mixture of said silicon carbide and silica.

2. A method according to claim 1, further comprising the step of drying said at least partially solidified spheres so as to provide dry spherical particles of said catalyst support.

3. A method according to claim 3 further comprising the step of calcining said dry spherical particles at a temperature of between about 350° C. to about 600° C. so as to provide calcined spherical particles.

4. A method according to claim 3, further comprising the step of hydrothermally treating said calcined spherical particles so as to provide said hydrothermally treated particles having an average pore diameter of at least about 150 Å.

5. A method according to claim 4, further comprising the step of calcining said hydrothermally treated particles at a temperature of between about 350° C. to about 600° C.

6. A method according to claim 5, wherein said catalyst support has a surface area of at least about 30 m$^2$/g and a particle size of at least about 0.1 mm.

7. A method according to claim 1, further comprising the step of adding a viscosity controlling agent to said suspension so as to provide said suspension with a viscosity of at least about 50 cp at 25° C.

8. A method according to claim 1, wherein the pore size controlling agent is selected from the group consisting of hexamethylenetetramine, urea, water soluble starch, and mixtures thereof.

9. A method according to claim 1, wherein said suspension has a pH of between about 9 to about 10.

10. A method according to claim 1, wherein said suspension forming step further comprises the steps of providing a colloidal suspension of said silica, providing said silicon carbide in the form of particles having a particle size of less than or equal to about 150 μm, and mixing said silicon carbide with said colloidal suspension.

11. A method according to claim 1, wherein said suspension forming step further comprises the steps of providing a colloidal suspension of said silica, providing said silicon carbide in the form of particles having a particle size of less than or equal to about 50 μm, and mixing said silicon carbide with said colloidal suspension.

12. A method according to claim 1, wherein said droplet forming step comprises forming droplets of said suspension having a droplet size of between about 0.1 mm to about 3.0 mm.

13. A method according to claim 1, further comprising the step of providing a two phase liquid system having an upper phase comprising said inert organic liquid phase and a lower phase comprising said aqueous acidic solution, and wherein said steps of passing said droplets and said spheres comprises the step of passing said droplets through said two phase liquid system.

14. A method according to claim 1, wherein said inert organic liquid phase is selected from the group consisting of kerosene, hexane, toluene, mineral oil, vegetable oil, alcohol and mixtures thereof.

15. A method according to claim 14, wherein said inert organic phase further comprises an anionic surfactant.

16. A method according to claim 1, wherein said aqueous acidic solution has a pH of between about 4 to about 5.

17. A method for preparing a catalyst system, comprising the steps of:

providing a catalyst support comprising substantially spherical particles of a substantially homogeneous mixture consisting of silicon carbide and silica, wherein said particles have a surface area of at least about 30 $m^2/g$ an average pore diameter of at least about 150 Å, and a particle size of at least about 0.1 mm;

supporting a catalytically active metal phase on said support comprising at least one metal selected from the group consisting of Group IVb metals, Group VIII metals, and mixtures thereof; and calcining said catalyst support and supported catalytically active phase at a temperature of between about 350° C. to about 600° C. so as to provide said catalyst system.

18. A method according to claim 17, wherein said supporting step comprises supporting a first metal selected from Group IVb and a second metal selected from Group VIII.

19. A method according to claim 17, wherein said first metal ius selected from the group consisting of zirconium, titanium, hafnium and mixtures thereof, and wherein said second metal is selected from the group consisting of cobalt, iron, nickel, ruthenium, and mixtures thereof.

20. A method according to claim 17, wherein said supporting step comprises impregnating said support with at least one aqueous solution of said at least one metal.

21. A method according to claim 20, wherein said at least one aqueous solution of said at least one metal comprises a solution in water of a water soluble salt of said at least one metal.

22. A method according to claim 21, wherein said water soluble salt is selected from the group consisting of nitrates, oxalates, sulfates, acetates, acetylacetanates, and mixtures thereof.

* * * * *

UNITED STATES PATENT AND TRADEMARK OFFICE
CERTIFICATE OF CORRECTION

PATENT NO. : 5,710,093
DATED : January 20, 1998
INVENTOR(S) : Luis A. Rivas et al.

It is certified that error appears in the above-identified patent and that said Letters Patent is hereby corrected as shown below:

In claim 3 the dependency should be changed from "3" to --2--.

Signed and Sealed this

Twenty-ninth Day of September, 1998

Attest:

BRUCE LEHMAN

*Attesting Officer*  *Commissioner of Patents and Trademarks*